US007875449B2

(12) United States Patent
Artursson et al.

(10) Patent No.: US 7,875,449 B2
(45) Date of Patent: Jan. 25, 2011

(54) OLIGONUCLEOTIDE NON-VIRAL DELIVERY SYSTEMS

(75) Inventors: Per Artur Sven Artursson, Uppsala (SE); Mohamed Mahmoud Issa, Uppsala (SE); Sabina Prochazkova Strand, Tiller (NO); Kjell Morten Varum, Trondheim (NO)

(73) Assignee: FMC Biopolymer AS, Drammen (NO)

( * ) Notice: Subject to any disclaimer, the term of this patent is extended or adjusted under 35 U.S.C. 154(b) by 77 days.

(21) Appl. No.: 11/855,193

(22) Filed: Sep. 14, 2007

(65) Prior Publication Data

US 2008/0131371 A1 Jun. 5, 2008

Related U.S. Application Data

(60) Provisional application No. 60/844,729, filed on Sep. 15, 2006.

(51) Int. Cl.
C12N 15/00 (2006.01)
(52) U.S. Cl. .................................................. 435/320.1
(58) Field of Classification Search ............... 435/320.1
See application file for complete search history.

(56) References Cited

U.S. PATENT DOCUMENTS

| | | | |
|---|---|---|---|
| 3,922,260 A * | 11/1975 | Peniston et al. ................ 536/20 |
| 6,184,037 B1 | 2/2001 | Roland et al. |
| 2003/0134810 A1 | 7/2003 | Springate et al. |
| 2003/0166594 A1 | 9/2003 | Blum et al. |
| 2005/0164964 A1 | 7/2005 | Artursson et al. |
| 2005/0170355 A1 | 8/2005 | Artursson et al. |
| 2007/0116767 A1 | 5/2007 | Mohapatra et al. |
| 2008/0085242 A1 | 4/2008 | Artursson et al. |
| 2009/0110719 A1* | 4/2009 | Roy et al. ................... 424/450 |

FOREIGN PATENT DOCUMENTS

| | | |
|---|---|---|
| WO | WO-03030941 A1 | 4/2003 |
| WO | WO-03092739 A1 | 11/2003 |
| WO | WO-03092740 A1 | 11/2003 |
| WO | WO-2004074314 A2 | 9/2004 |
| WO | WO-2005113770 A1 | 12/2005 |
| WO | WO-2007050643 A1 | 5/2007 |
| WO | WO-2007059605 A1 | 5/2007 |
| WO | WO-2008003329 A2 | 1/2008 |

OTHER PUBLICATIONS

Koping-Hoggard M et al., "Improved chitosan-mediated gene delivery based on easily dissociated chitosan polyplexes of highly defined chitosan oligomers", Gene Therapy, Nature Publishing Group, vol. 11 No. 19 Oct. 2004 pp. 1441-1452. XP-002471182 ISSN: 0969-7128.
Katas H et al., "Development and characterisation of chitosan nanoparticles for siRNA delivery", Journal of Controlled Release. Elsevier Science Publishers BV, Amsterdam NL vol. 115 No. 2 Oct. 2006 pp. 216-225 XP005705694 ISSN: 0168-3659 Available online Jul. 25, 2006.
Gao S, et al., "Targeting delivery of oligonucleotide and plasmid DNA to hepatocyte via galactosylated chitosan vector" European Journal of Pharmaceutics and BioPharmaceuticals, Elsevier Science Publishers BV. Amsterdam NL vol. 60 No. 3 Aug. 2005 pp. 327-334, XP004967314 ISSN: 0939-6411.
Lavertu et al., "High efficiency gene transfer using chitosan/DNA nanoparticles with specific combinations of molecular weight and degree of acetylation" Biomaterials, Elsevier Science Publishers BV, Barking GB, vol. 27 No. 27 Sep. 2006 pp. 4815-4824, XP005495427 ISSN: 0142-9612 Available online May 24, 2006.
Issa M M "Linear and Branched Chitosan Oligomers as Delivery Systems for pDNA and siRNA in vitro and in vivo" Nov 29, 2006 Uppsala University, Uppsala SE XP002471183 ISSN: 1651-6192 ISBN: 91-554-6747-4.
Notification of Transmittal of the International Search Report and the Written Opinion of the International Searching Authority, or the Declaration—Dated Mar. 17, 2008—International Application No. PCT/EP2007/059740—International Filing Date—Sep. 14, 2007.
Meister G, et al., "Mechanisms of Gene Silencing by Double-stranded RNA" Nature 431(7006) (2004) pp. 343-349. Nature Publishing Group.
Sachse C, et al., "High-throughput RNA interference strategies for target discovery and validation by using synthetic short interfering RNAs: functional genomics investigations of biological pathways" Methods Enzymology 392(2005) pp. 242-277. Elsevier Inc.
Cejka D, et al. "Short interfering RNA (siRNA): tool or therapeutic?" Clinical Science. 110(1) (2006) 47-58. London, Great Britain.
Burkhardt B R, et al. "Efficient delivery of siRNA into cytokine-stimulated insulinoma cells silences Fas expression and inhibits Fas-mediated apoptosis" Federation of European Biochemical Societies Letters 580(2) (2006) pp. 553-560, Elsevier BV.
Devi GR "siRNA-based approaches in cancer therapy" Cancer Gene Therapy, (2006). 13PP 819-829 Nature Publishing Group published online Jan. 2, 2006.
Nishitsuji H, et al, "Effective Suppression of Human Immunodeficiency Virus Type 1 through a Combination of Short- or Long-Hairpin RNAs Targeting Essential Sequences for Retroviral Integration" J Virology. 80(15) (Aug. 2006) pp. 7658-7666. America Society for Microbiology.
Elman J, et al. "Locked nucleic acid (LNA) mediated improvements in siRNA stability and functionality" Nucleic Acids Res. 33(1) (2005) pp. 439-447 Oxford University Press.
Chen X., et al. "Chemical modification of gene silencing oligonucleotides for drug discovery and development" Drug Discovery Today. 10(8) (Apr. 2005) pp. 587-593.

(Continued)

Primary Examiner—Brian Whiteman
(74) Attorney, Agent, or Firm—FMC Corporation

(57) ABSTRACT

Low molecular weight low molecular weight chitosan oligomers were able to self-assemble siRNA into nanosized particles, provide protection against enzymatic degradation, and mediate gene silencing that is stable over a long period of time in vitro. The control of structural variables in formulating complexes of siRNA with low molecular weight chitosans provides an efficient alternative delivery system for siRNA in vitro and in vivo.

11 Claims, 7 Drawing Sheets

OTHER PUBLICATIONS

Figure 1:
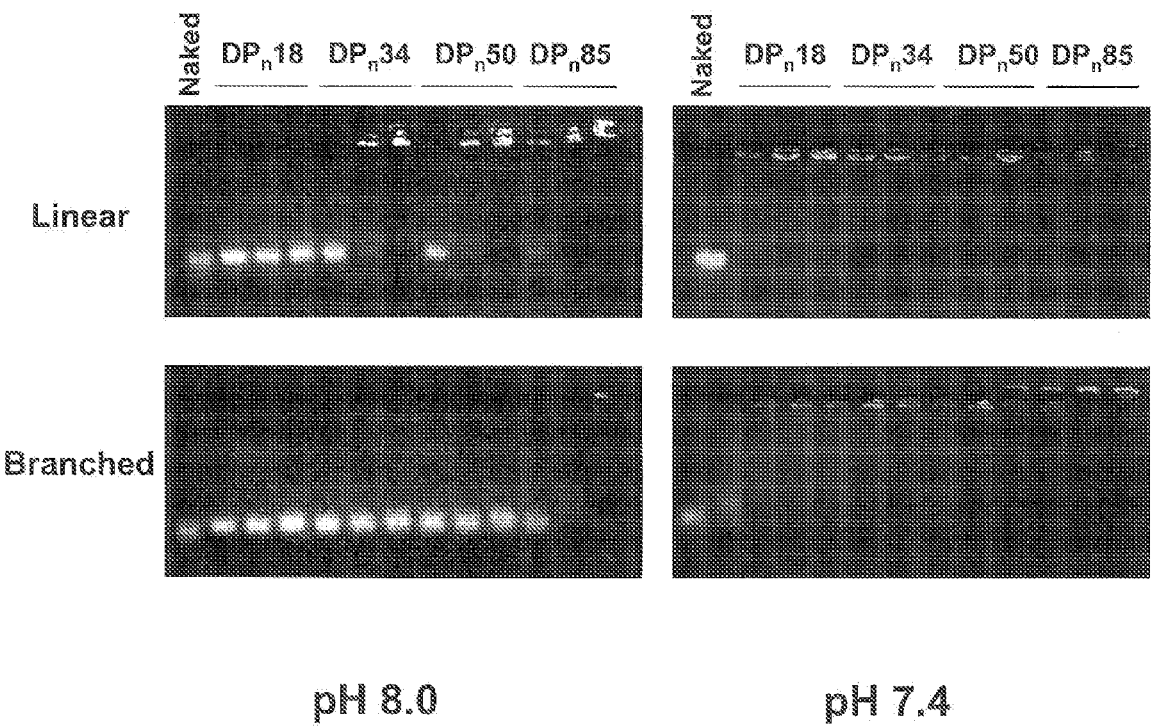
Figure 1:
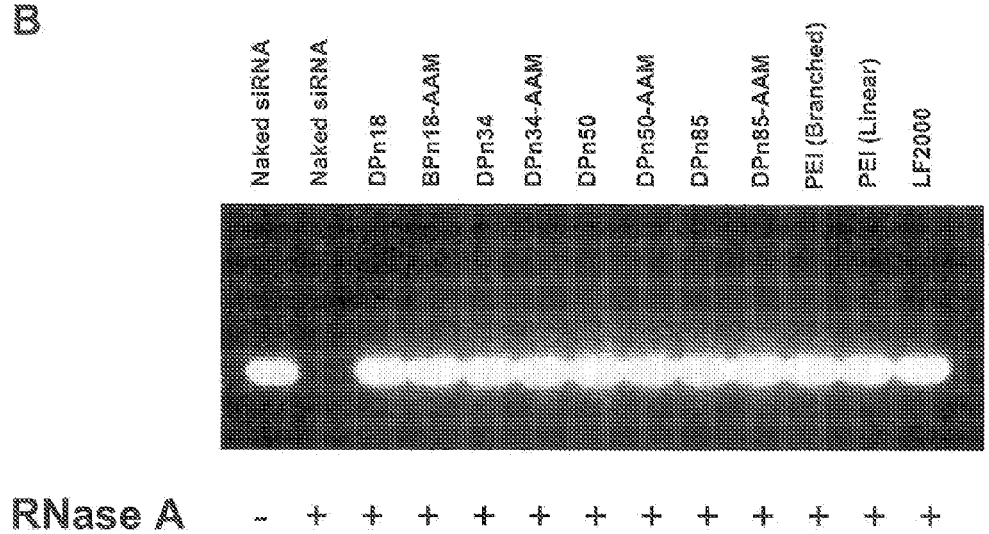

Lorenz C, et al. "Steroid and lipid conjugates of siRNAs to enhance cellular uptake and gene silencing in liver cells" Bioorganic & Medicinal Chemistry Letters 14(19) (2004) pp. 4975-4977. Elsevier Ltd.

Dalby B, et al. "Advanced transfection with Lipofectamine 2000 reagent: primary neurons, siRNA, and high-throughput applications" Methods. 33(2) (2004) pp. 95-103 Elsevier Inc.

Hassani Z, et al "Lipid-mediated siRNA delivery down-regulates exogenous gene expression in the mouse brain at picomolar levels" J Gene Medicine 7(2) (2005) pp. 198-207. Published online Oct. 28, 2004 John Wiley & Sons, Ltd.

Urban-Klein B, et al. "RNAi-mediated gene-targeting through systemic application of polyethylenimine (PEI)-complexed siRNA in vivo" Gene Therapy 12(5) (2005) pp. 461-466 Nature Publishing Group published online Dec. 23, 2004.

Zhou J, et al. "PAMAM dendrimers for efficient siRNA delivery and potent gene silencing" Chem Commun (Camb).22) (2006) pp. 2362-2364 Royal Society of Chemistry, published as an Advance Article online May 10, 2006.

Leng Q, et al. "Highly branched HK peptides are effective carriers of siRNA" J Gene Medicine 7(7) (2005) pp. 977-986 John Wiley & Sons published online Mar. 17, 2005.

Chen HT et al. Cytotoxicity, hemolysis, and acute in vivo toxicity of dendrimers based on melamine, candidate vehicles for drug delivery, J American Chemical Society 126(32) (2004) pp. 10044-10048. Published on web Jul. 22, 2004.

Roy K, et al. "Oral gene delivery with chitosan-DNA nanoparticles generates immunologic protection in a murine model of peanut allergy" Nature Medicine 5(4) (Apr. 1999) pp. 387-391.

Koping-Hoggard M, et al. "Chitosan as a nonviral gene delivery system. Structure- property relationships and characteristics compared with polyethylenimine in vitro and after lung administration in vivo" Gene Therapy 8(14) (2001) pp. 1108-1121 Nature Publishing Group.

Zhang W, et al. "Inhibition of respiratory syncytial virus infection with intranasal siRNA nanoparticles targeting the viral NS1 gene" Nature Medicine 11(1) (Jan. 2005) pp. 56-62. Published online Dec. 26, 2004.

Elbashir S M, et al. Duplexes of 21-nucleotide RNAs mediate RNA interference in cultured mammalian cells, Nature. 411(May 24, 2001) pp. 494-498. Macmillan Magazines Ltd.

Honkakoski P, et al. "A novel drug-regulated gene expression system based on the nuclear receptor constitutive androstane receptor (CAR)", Pharmaceutical Research. 18(2) (2001) pp. 146-150 Plenum Publishing Corp.

Lappalainen K., et al. "Comparison of cell proliferation and toxicity assays using two catonic liposomes" Pharmaceutical Research 11(8) (1994) pp. 1127-1131 Plenum Publishing Corp.

Janes K A, et al. "Polysaccharide colloidal particles as delivery systems for macromolecules" Advanced Drug Delivery Reviews 47(1) (2001) pp. 83-97 Elsevier Science BV.

Liu X., et al. "The influence of polymeric properties on chitosan/siRNA nanoparticle formulation and gene silencing" Biomaterials 28 (2007) 1280-1288 Elsevier Ltd.

Issa M M, et al. Chitosan Oligomers as siRNA delivery systems in vitro ASGT abstract 1023 Poster Session III: Oligonucleiotide Therapies II Jun. 2, 2007.

Tommeraas K, et al. "Preparation and characterization of chitosans with oligosaccharide branches" Carbohydrate Research vol. 337 (2002) pp. 2455-2462 Elsevier Science Ltd.

Strand S P, et al. "Influence of chitosan structure on the formation and stability of DNA-chitosan polyelectrolyte complexes" Biomacromolecules Nov.-Dec. 2005;6(6): pp. 3357-3366 American Chemical Society.

Koping-Hoggard M, et al. "Relationship between the physical shape and the efficiency of oligomeric chitosan as a gene delivery system in vitro and in vivo" Journal of Gene Medicine 2003 5 pp. 130-141 John Wiley & Sons.

\* cited by examiner

A

B

OLIGONUCLEOTIDE NON-VIRAL DELIVERY SYSTEMS

This application claims the benefit of U.S. Provisional Application No. 60/844,729, filed Sep. 15, 2006.

FIELD OF THE INVENTION

The present invention relates generally to the fields of nucleic acid delivery and gene expression. In particular, the present invention relates to a new non-viral delivery system for oligonucleotides, especially small interfering RNA (siRNA).

BACKGROUND OF THE INVENTION

RNA interference (RNAi) is a natural mechanism involving specific down regulation of target gene expression by double-stranded short interfering RNA (siRNA) [1]. RNAi has increasingly become a well-established tool in functional genomics and in target screening and validation in vitro [2, 3]. More importantly, the development of siRNA-based drugs holds promise in finding therapies for complex diseases such as diabetes, cancer, and viral infections [4-7].

As for other forms of nucleic acids such as plasmid DNA (pDNA), poor serum stability, unfavorable pharmacokinetics in vivo, and inefficient cellular uptake remain the main challenges for successful gene silencing applications [8]. One strategy to partly overcome such problems is the use of chemically modified siRNAs that exhibit resistance to nuclease degradation as well as improved cellular uptake [9-11]. Another strategy involves the use of polycation-based siRNA formulations. For instance, cationic lipid-based formulations were shown to be effective for in vitro and in vivo delivery of siRNA [12-15]. In contrast, cationic polymers were initially considered unsuitable for oligonucleotides delivery [16]. However, recent studies have shown that cationic polymers such as polyethyleneimine (PEI), polyamidoamine (PAMAM) dendrimers and poly-L-lysine (PLL) can be used for siRNA delivery [17-19]. Contradictory accounts on the efficiency of cationic polymers as delivery systems for oligonucleotides were formulated and delivered under conditions optimized for pDNA. Furthermore, several reports have raised concerns about the in vivo toxicity of the above mentioned polycations, which may hamper their future clinical applications [20-22]. Therefore, the search for non-toxic, efficient vectors for siRNA delivery is motivated.

SUMMARY OF THE INVENTION

The invention encompasses a composition comprising complexes of: (a) low molecular weight chitosan having a number average Degree of Polymerization (DPn) in the range between 30 and 300 and where the degree of deacetylation of the low molecular weight chitosan is greater than 90%; and (b) an oligonucleotide. The composition of claim 1, includes a low molecular weight chitosan obtained from high molecular weight chitosan using chemical or enzymatic methods. The degree of deacetylation of the low molecular weight chitosan is greater than 95%, and most preferably greater than 99%. Additionally, the composition essentially has a net positive charge ratio. The low molecular weight chitosan is derivatized with targeting ligands and stabilizing agents. The oligonucleotide comprises a silencing sequence that will express its function when introduced into a host cell. The oligonucleotide is selected from the group consisting of RNA molecules, antisense molecules, Ribozymes, and micro RNAs. The composition of the invention has a pH in the range of 3.5 to 8.0, more preferably in the range of 7.1 to 7.6.

The invention also encompasses method of preparing the inventive composition comprising the steps of:
(a) exposing the low molecular weight chitosan to an aqueous solvent; (b) mixing the aqueous solution of step (a) with an oligonucleotide in an aqueous solvent; and (c) maintaining the pH of the composition in the range of 3.5-8.0, more preferably in the range of 7.1 to 7.6. The invention also contemplates the method of preparing the composition in which after step (b) the volume of the product solution produced in step (b) is reduced to obtain a desired concentration of the composition.

The invention also encompasses a method of administering nucleic acid to a mammal, comprising using the disclosed composition and introducing the composition into the mammal. The method of introducing the composition into the mammal is accomplished by administration to mucosal tissues by pulmonary, nasal, oral, ocular, buccal, sublingual, topical, rectal, or vaginal routes. Alternatively, the composition is introduced into the mammal by administration to submucosal tissues by parenteral routes that are intravenous, intramuscular, intradermal, intracranial, intraspinal, subcutaneous, or intracardiac, or administered to internal organs, blood vessels, or other body surfaces or body cavities exposed during surgery. The inventive method includes administering the disclosed composition to a mammal, whereby the oligonucleotide is capable of expressing its function inside at least one cell of the mammal. The invention also encompasses a method of using the disclosed composition prepared as a medicament for prophylactic or therapeutic treatment of a mammal. These uses include but are not limited to gene therapy, antisense therapy, or genetic vaccination for prophylactic or therapeutic treatment of malignancies, autoimmune diseases, inherited disorders, pathogenic infections and other pathological diseases. Furthermore, the invention encompasses using the disclosed composition as a diagnostic agent for use in in vivo or in vitro diagnostic methods.

BRIEF DESCRIPTION OF THE DRAWINGS AND THE SEQUENCE LISTING

FIG. 1 shows the physical stability (A) and RNase A protection (B) of siRNA formulations. siRNA complexes formulated with linear $DP_n85$ chitosans displayed the highest physical stability at both the pH values and at all the charge ratios tested. All the selected polycations were able to protect the siRNA from enzymatic degradation by RNase A. For the agarose gel electrophoresis, 100 ng siRNA was loaded into each well. Complexes were formulated at charge ratios of 30:1 (+/−) and 60:1 (+/−) for chitosan $DP_n18$ formulations. A charge ratio of 15:1 (+/−) was used for PEI formulations, while complexes of siRNA with lipofectamine 2000 were formulated at a weight ratio of 2:1 (+/−). Representative gels from three independent experiments are shown.

Figure 2:
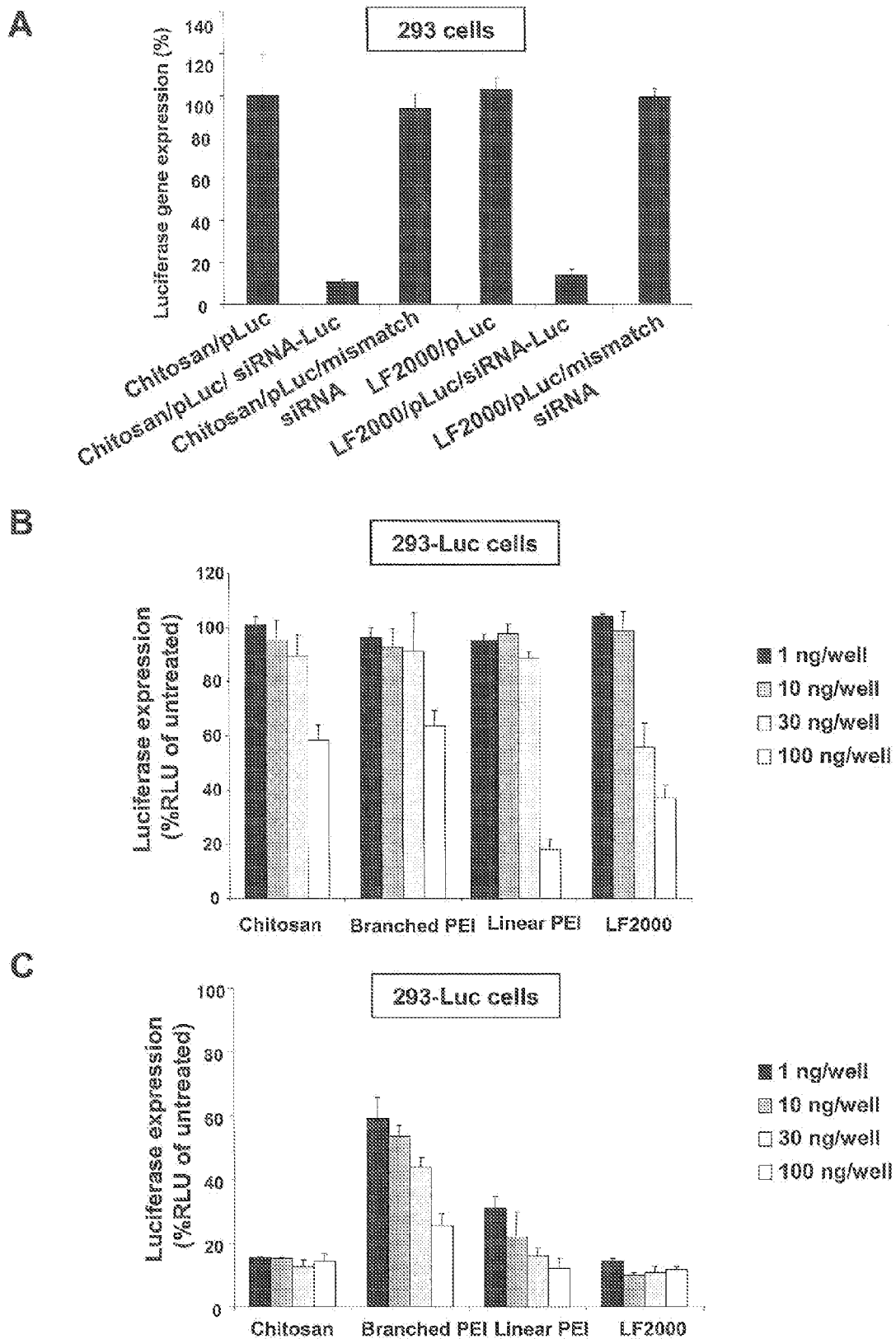

FIG. 2 shows in vitro delivery of siRNA in normal HEK 293 cells (A) and in stably luciferase-expressing HEK 293 cells (293-Luc) (B, C). Significant luciferase silencing was achieved when the specific siRNA-Luc was co-transfected with pLuc (A) or pGFP (C) compared with the control untreated cells. Reduced efficiency of luciferase inhibition was obtained when siRNA-Luc was solely delivered to 293-Luc cells (B). Luciferase gene expression was analyzed 48 h after transfection. Chitosans previously optimized for pDNA delivery were used (branched $DP_n34$) [27] to form complexes with siRNA formulated at a charge ratio of 10:1. A charge ratio of 5:1 (+/−) was used for PEI complexes, while complexes of siRNA with LF 2000 were formulated at a weight ratio of 2:1 (+/−). The gene expression results are expressed as mean values±S.D.; n=4.

Figure 3:
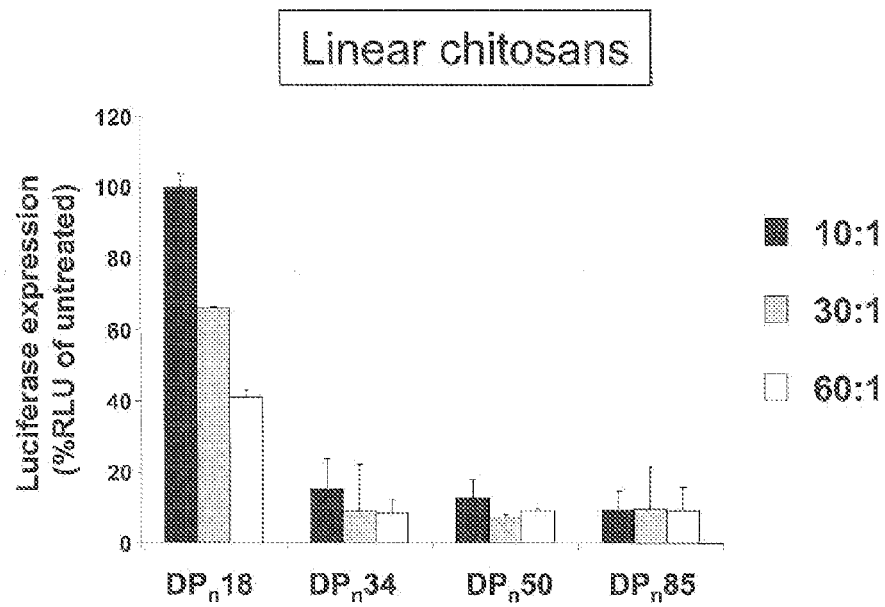
Figure 3:
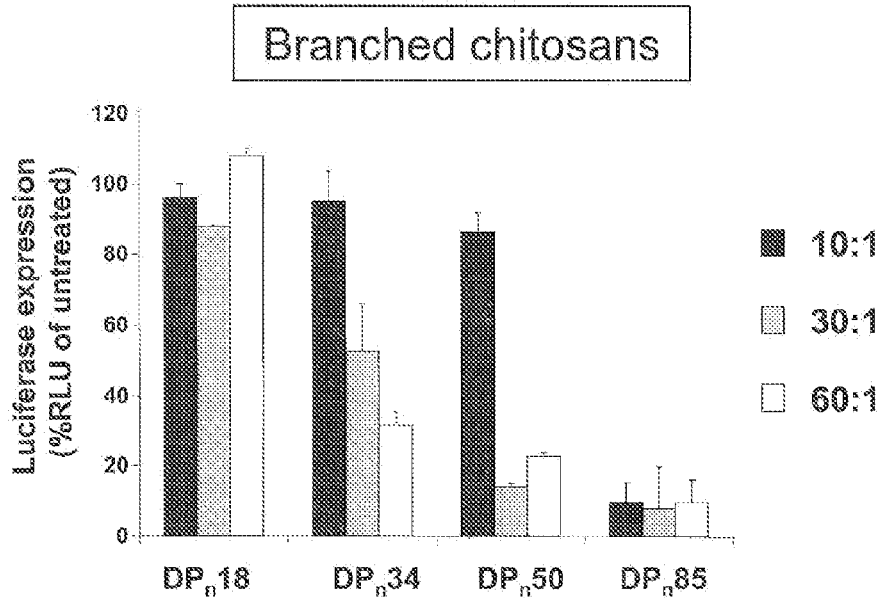

FIG. 3 shows the influence of the structural variables of linear (A) and branched (B) chitosan complexed with oligonucleotides on the luciferase silencing activity in 293-Luc cells. While the chain length and the charge ratio seemed not to be critical for complexes formed with linear chitosan having chain lengths longer than 34 monomer units (number average degree of polymerization higher than 34 monomer units), efficient luciferase silencing mediated by the branched chitosan complexes required higher charge density in terms of longer chitosan chain lengths and higher charge ratios. A siRNA concentration of 150 nM (100 ng/well) was used. Luciferase gene expression was analyzed 48 h after transfection. Chitosan complexes were formulated at charge ratios of 30:1 (+/−). The gene expression results are expressed as mean values±S.D.; n=4.

Figure 4:
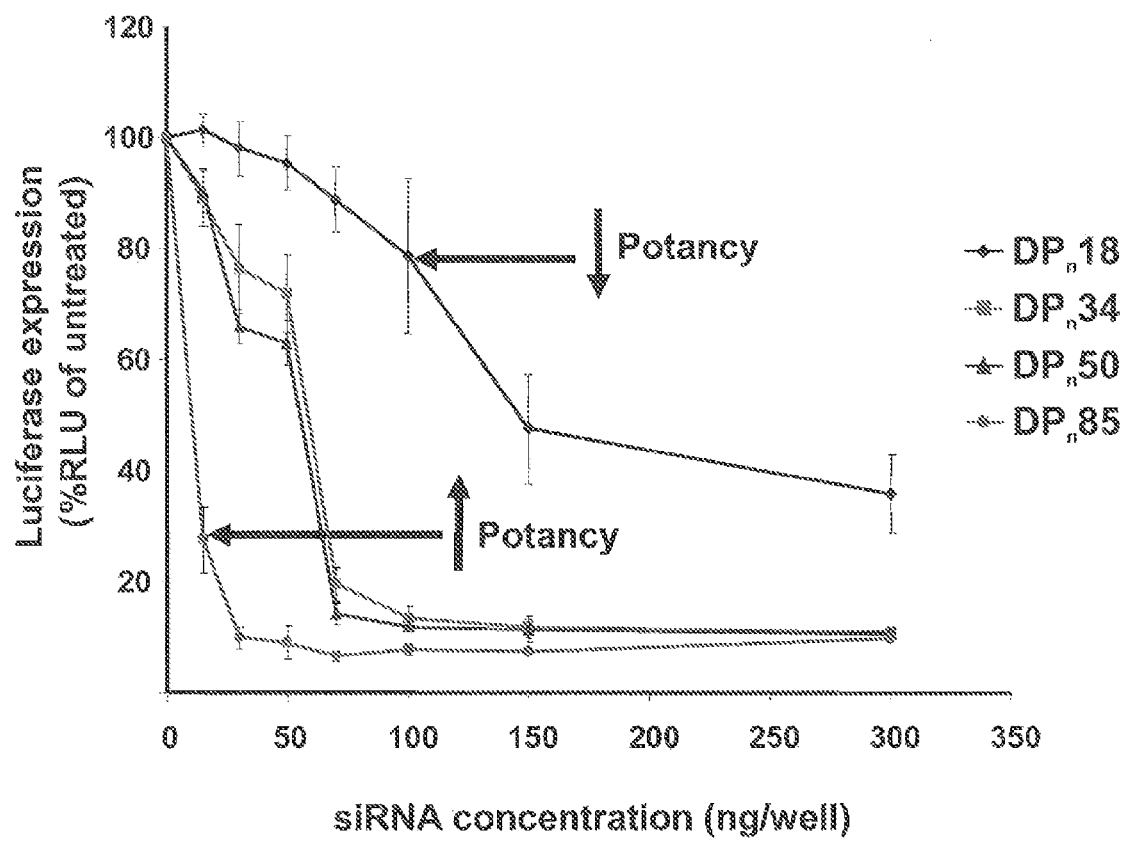

FIG. 4 shows siRNA concentration dependency and relative efficiency of linear low molecular weight chitosans. At lower siRNA concentrations (15-30 ng/well, equivalent to siRNA concentration of 22-44 nM/well), linear $DP_n85$ low molecular weight chitosans demonstrated the highest potency by knocking down the luciferase expression by 72-95% of the control untreated 293-Luc cells. Luciferase gene expression was analyzed 48 h after transfection. Chitosan complexes were formulated at charge ratios of 30:1 (+/−). The gene expression results are expressed as mean values±S.D.; n=4.

Figure 5:
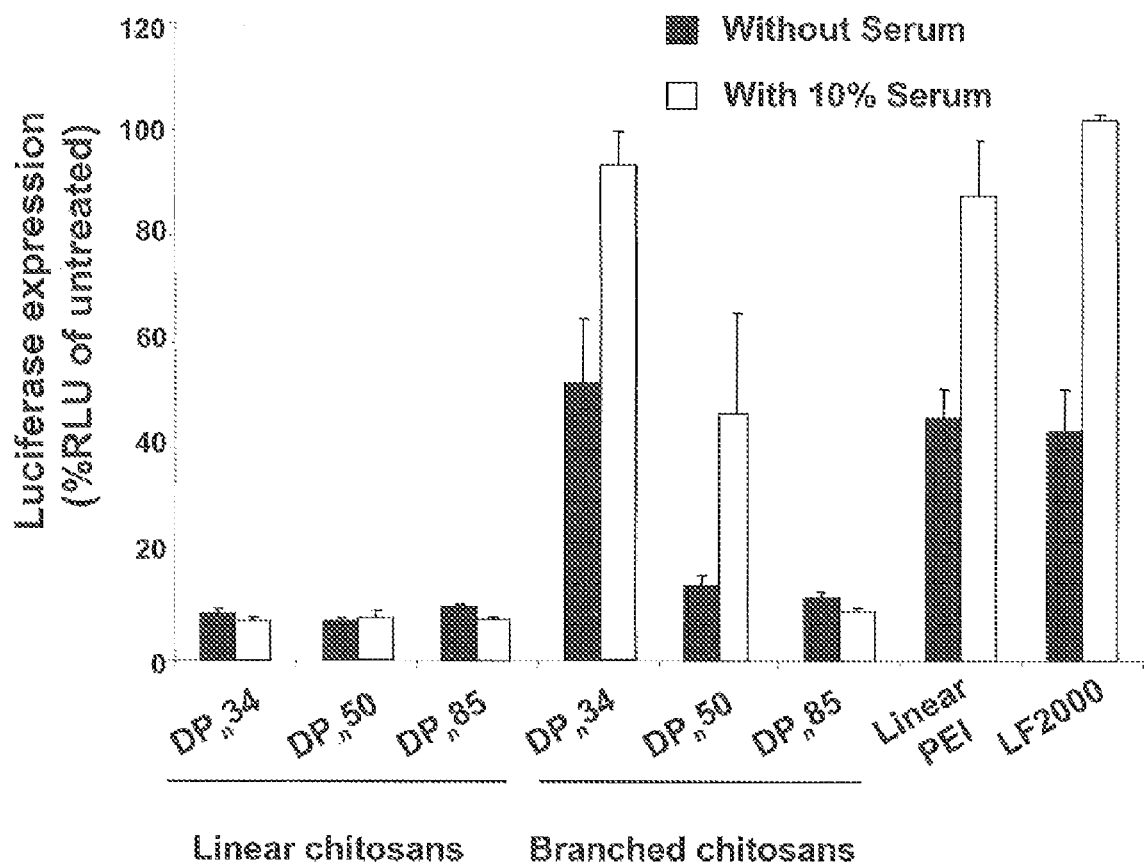

FIG. 5 illustrates the effect of serum on the luciferase silencing activity. Among the various polycation formulations tested, all linear chitosans and branched $DP_n85$ retained their luciferase silencing activity in 293-Luc cells in the presence of 10% serum in the transfection medium. A siRNA concentration of 150 nM was used. Luciferase gene expression was analyzed 48 h after transfection. siRNA complexes were formulated at charge ratios of 30:1 and 15:1 (+/−) for Low molecular weight chitosans and PEI, respectively. Complexes of siRNA with LF2000 were formulated at a weight ratio of 2:1 (+/−). The gene expression results are expressed as mean values±S.D.; n=4.

Figure 6:
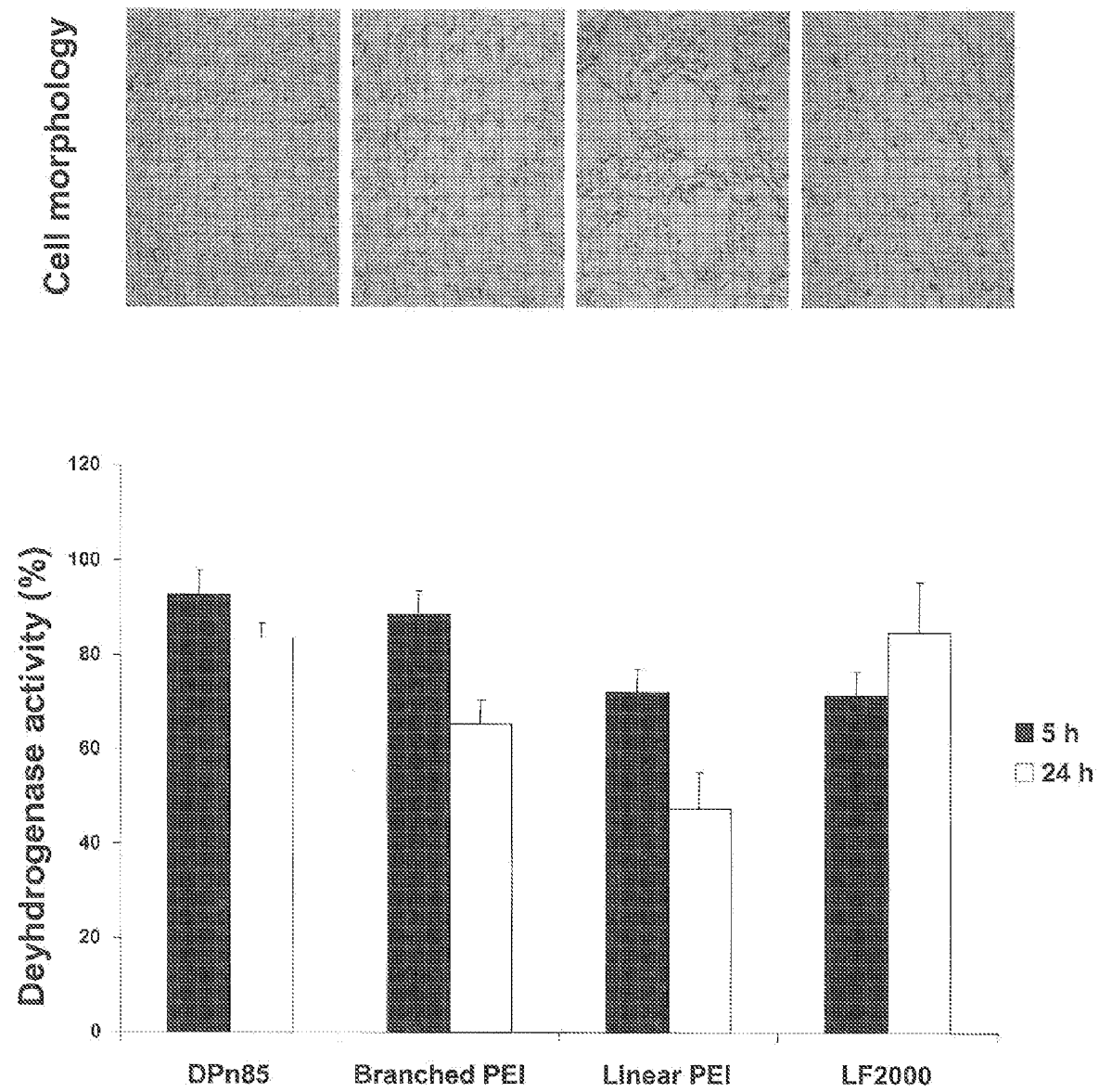

FIG. 6 illustrates the cellular toxicity of siRNA formulations. Intracellular dehydrogenase activity (a measure of cell toxicity) was determined by the MTT method directly or 24 h following transfection of 293-Luc cells with various siRNA formulations. In contrast to PEI and LF2000, both the cell morphology and the intracellular dehydrogenase activity were retained following transfection with siRNA complexes formulated with linear $DP_n85$. Although LF2000 complexes displayed significant toxicity directly following transfection, cell viability was restored after 24 h of transfection. A siRNA concentration of 150 nM was used. siRNA complexes were formulated at charge ratios of 30:1 and 15:1 (+/−) for low molecular weight chitosans and PEI, respectively. Complexes of siRNA with LF2000 were formulated at a weight ratio of 2:1 (+/−). The gene expression results are expressed as mean values±S.D.; n=4-5.

Figure 7:
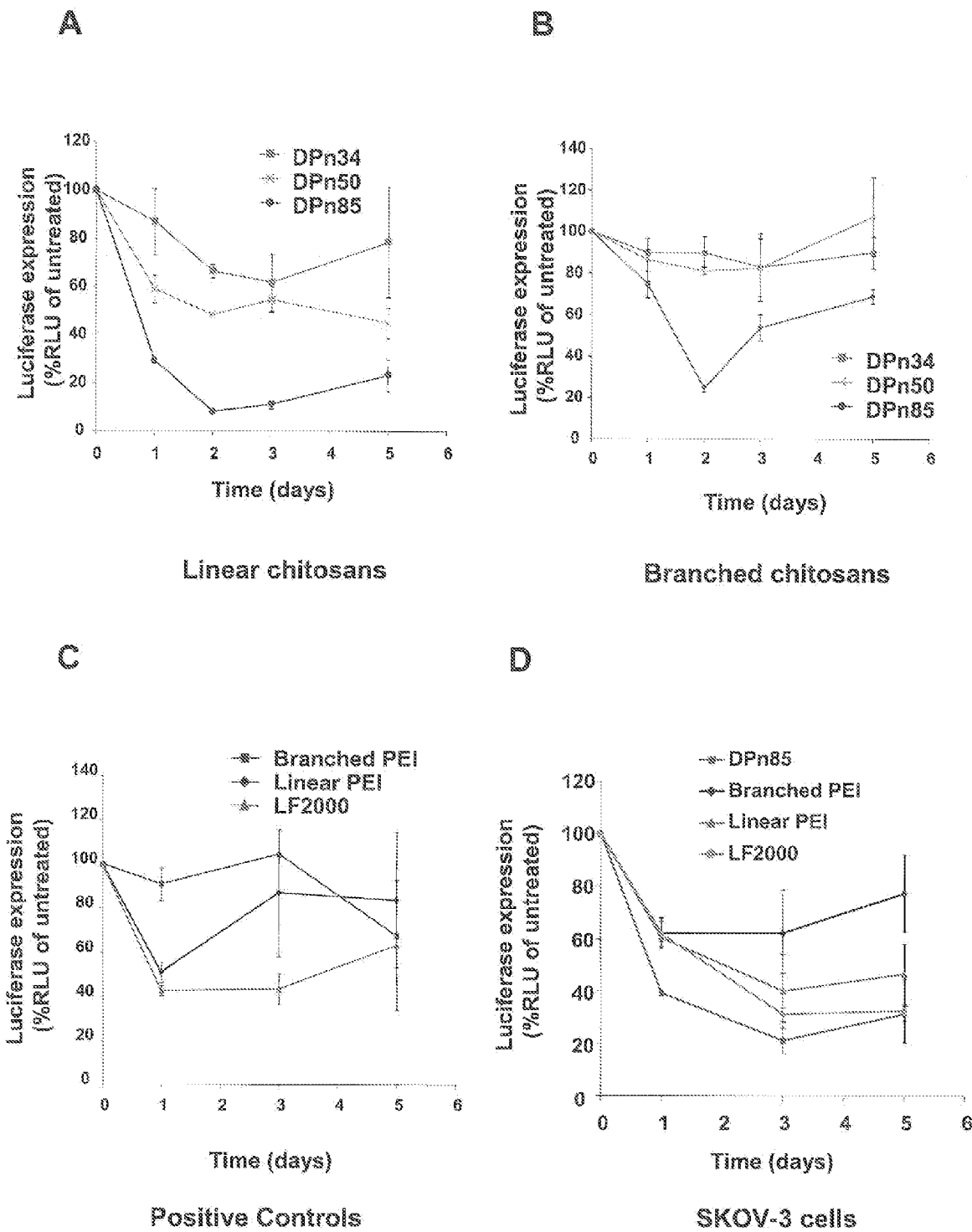

FIG. 7 shows the time course of the luciferase silencing in 293-Luc cells (A, B, C) and in stably luciferase-expressing SKOV-3 cells (D) in vitro. In both 293-Luc and SKOV-3-Luc cells, linear chitosan with $DP_n85$ displayed the best luciferase silencing kinetics in terms of earlier onset and sustained luciferase silencing that lasted for 5 days, suggesting a stable release of intact siRNA intracellularly. A siRNA concentration of 44 nM (30 ng/well) was used. siRNA complexes were formulated at charge ratios of 30:1 and 15:1 (+/−) for low molecular weight chitosans and PEI, respectively. Complexes of siRNA with LF2000 were formulated at a weight ratio of 2:1 (+/−). The gene expression results are expressed as mean values±S.D.; n=4.

BRIEF DESCRIPTION OF THE SEQUENCE LISTING

SEQ ID NO. 1: siGL3 (sense, 5'-CUUACGCUGAGUACU-UCGAdTdT-3';
SEQ ID NO. 2: antisense, 5'-UCGAAGUACU-CAGCGUAAGdTdT-3') is an unmodified siRNA duplex that targets the luciferase gene (siRNA-Luc), ordered from MedProbe (Lund, Sweden) [28].
SEQ ID NO.3: A mismatching siRNA; siCONTROL non-targeting siRNA #1 (siCON1; sense, 5'-UAGCGAC-UAAACACAUCAAUU-3';
SEQ ID NO. 4: antisense, 5'-UUGAUGUGUUUAGUCGC-UAUU-3'), was ordered from Dharmacon Research, Inc. (Lafayette, Colo.).

DETAILED DESCRIPTION OF THE INVENTION

Chitosans, a family of linear binary polysaccharides comprised of (1-4) linked 2-amino-2-deoxy-β-D-glucose (GlcN) and the N-acetylated analogue 2-acetamido-2-deoxy-β-D-glucose (GlcNAc) are biocompatible cationic polymers, and have been shown to be suitable for plasmid pDNA gene delivery [23-27]. Quite effective gene delivery in vitro and in vivo has been obtained with linear and branched chitosan oligomers of well-defined molecular weight distributions [25, 27]. The chitosan-oligomer-based complexes had improved physical properties including reduced viscosity and were less prone to aggregation. These complexes also possessed improved efficiency including improved cellular uptake, early onset, and high levels of in vivo gene expression.

In the instant invention, the potential low molecular weight (7-17 kDa), essentially fully deacetylated (greater than 99% deacetylated) chitosans in novel siRNA delivery systems is realized. Using lipofectamine 2000 (LF2000) and PEI (linear and branched) as controls, the physical stability and the resistance against RNase degradation of siRNA complexes formulated with low molecular weight chitosans was investigated. In most reports on siRNA delivery, a co-transfection method is used to incorporate a non-physiologically relevant target or an irrelevant pDNA in the siRNA formulations. Therefore, we first examined the effect of such incorporation on the efficiency of siRNA delivery by various polycations in stably luciferase-expressing cell lines in vitro. We then investigated formulation and structure in complexes of siRNA formulation and low molecular weight chitosans. More specifically, the role of the structural variables of low molecular weight chitosans (chain length and branching), the formulation parameters (charge ratios, siRNA concentrations), and the effect of serum were studied and correlated to the efficiency of the gene silencing activity in vitro. The cellular toxicity of various siRNA formulations was compared as was the in vitro kinetics of luciferase gene silencing.

This work demonstrates the potential of low molecular weight chitosan as novel delivery systems for small interfering RNA (siRNA). Using polyethyleneimine (PEI) and lipofectamine 2000 (LF2000) as controls, chitosan of various chain lengths were complexed with siRNA and their physical stability and protection against enzymatic degradation were examined. The cellular toxicity and luciferase gene silencing activity of the siRNA complexes were investigated in stably luciferase-expressing 293 cells (293-Luc) in vitro. The effects of chitosan structural variables as well as the formulation parameters on the luciferase silencing activity of siRNA complexes were also studied. Low molecular weight chitosans were able to complex siRNA into physically stable, nanoparticles (34-86 nm) that provided protection against RNase degradation. The importance of a higher number of positive charges provided by longer chitosan chain and/or higher charge ratios between of low molecular weight chitosans and siRNA was shown for mediating the highest luciferase silencing activity in vitro. Unlike PEI and LF2000, siRNA complexes formulated with low molecular weight chitosans retained their luciferase silencing activity transfection medium contained 10% serum. Low molecular weight chitosans also displayed minimal cellular toxicity compared to PEI and LF2000. Low molecular weight chitosans having a number-average degree of polymerization ($DP_n$) of 85 monomer units ($DP_n85$) required a siRNA concentration as low as 44 nM to obtain 95% silencing of the luciferase gene expression that was sustained for 5 days in 293-Luc cells. Taken together, our findings demonstrate low molecular weight chitosans as an efficient alternative delivery system for siRNA. We previously reported that essentially fully deacetylated low molecular weight chitosans of quite short chain lengths (18-34 monomer units) were optimal for the delivery of pDNA in vitro and in vivo [25, 27]. In the instant work, we report on the structure-property relationships of essentially fully deacetylated chitosan oligomers as siRNA delivery systems in vitro. For this purpose, linear and trisaccharide-substituted (branched) chitosan oligomers of carious chain lengths were selected. We found that, in contrast to pDNA delivery, linear chitosan oligonucleotides longer than 34 monomer units formed physically stable complexes with siRNA and mediated the highest luciferase silencing activity in luciferase-expressing HEK 293 (293-Luc) cells in vitro. Apparently, the structure-property relationships are quite different between siRNA and pDNA. This difference may be explained in that siRNA molecules are shorter, less flexible, and have a lower negative charge density compared to pDNA. Therefore, the complexation of siRNA into physically stable and efficient nanoparticles requires stronger ionic interaction with polycations [18, 33].

The particle size of the siRNA complexes formulated with essentially fully deacetylated low molecular weight chitosans in our work (less than 100 nm) was unexpectedly much smaller than those previously reported for lipids, PLL, and high molecular weight chitosans (85% deacetylation) [33, 34]. This can be attributed to the higher charge density on the essentially fully deacetylated chitosan backbone. In addition, the enhanced solubility and reduced viscosity of the low molecular weight chitosan may contribute to the small particle sizes of the siRNA complexes [35]. In agreement with previous findings, the co-transfection of the siRNA-Luc together with an irrelevant pDNA (pGFP) as a single package resulted in a significant luciferase silencing activity in 293-Luc cells in vitro [17]. However, we showed that the gene silencing activity was significantly compromised when the pDNA was excluded from the siRNA formulations. We conclude, therefore, that the presence of pDNA, a macromolecule with a high negative charge density significantly contributed to the efficiency of siRNA complexation with various polycations via improved cooperative interactions.

We also showed that a high charge density in terms of longer chitosan chains and/or higher charge ratios will not only yield physically stable complexes but also obtain the most efficient gene silencing in vitro. Our findings are in good agreement with previous results reported for PAMAM dendrimers, where higher generation numbers, higher charge ratios, and higher siRNA concentrations (100 nM) were required for better complexation and gene silencing activity obtained by siRNA/dendrimers complexes [18]. A similar high concentration of siRNA was also recommended for LF2000-based formulations [12]. In this instant invention, the most efficient low molecular weight chitosans (linear $DP_n85$) required a siRNA concentration as low as 44 nM to obtain more than 95% silencing of the luciferase gene expression in 293-Luc cells.

Moreover, under the experimental conditions in this work, siRNA complexes formulated with long, linear low molecular weight chitosans retained their luciferase silencing activity in the presence of 10% serum in the transfection medium. The most likely reason for the retained silencing activity may be that these complexes, in contrast to PEI and LF2000, can resist aggregation in such relatively high serum concentration, which may reflect an enhanced colloidal stability. The finding that shorter and branched chitosan oligomers demonstrated reduced gene silencing activity could be explained by the impaired siRNA complexation as a result of the reduced charge density and the steric hindrance of the charge interaction between the chitosan backbone and siRNA.

In agreement with the minimal cellular toxicity reported of siRNA complexes formulated with high molecular weight chitosans, we showed in this work that 293-Luc cells retained their intracellular dehydrogenase activity following transfection with $DP_n85$ low molecular weight chitosans even when a high siRNA concentration (150 nM) was used in the formulation [33]. Low molecular weight chitosans displayed a much lower cellular toxicity compared to previously published results on PAMAM dendrimers where the use of siRNA concentrations of 50-100 nM has lead to a significant reduction in cell viability (60-50%).

Finally, siRNA complexes formulated with linear low molecular weight chitosans displayed earlier onset and sustained luciferase silencing activity compared to those previously reported for PEI [17]. The improved kinetics of $DP_n85$ chitosan oligonucleotides is assumed to be a result of the improved cellular uptake of the small, nano-sized siRNA complexes and the sustained release of intact siRNA intracellularly.

2. Materials and Methods 2.1. Materials

A GMP-grade plasmid (gWiz™) containing a cytomegalovirus promoter and a firefly luciferase (pLuc) or green fluorescence protein (pGFP) was purchased from Aldevron, Fargo, N. Dak., USA. Lipofectamine 2000 (LF2000) was purchased from Invitrogen. Linear PEI; ExGen 500 (molecular weight of 22 kDa) was purchased from Ferementas, Germany. Branched PEI (molecular weight of 25 kDa) was purchased from Aldrich Sweden, Stockholm, Sweden.

2.2. siRNA Duplexes

SEQ ID NO. 1: siGL3 (sense, 5'-CUUACGCUGAGUACU-UCGAdTdT-3';

SEQ ID NO. 2: antisense, 5'-UCGAAGUACU-CAGCGUAAGdTdT-3') is an unmodified siRNA duplex that targets the luciferase gene (siRNA-Luc), ordered from MedProbe (Lund, Sweden) [28].

SEQ ID NO.3: A mismatching siRNA; siCONTROL non-targeting siRNA #1 (siCON1; sense, 5'-UAGCGAC-UAAACACAUCAAUU-3';

SEQ ID NO. 4: antisense, 5'-UUGAUGUGUUUAGUCGC-UAUU-3'), was ordered from Dharmacon Research, Inc. (Lafayette, Colo.).

2.3. Low Molecular Weight Chitosans

Fully de-N-acetylated (degree of deacetylation>99.8%; $F_A<0.001$) linear and 7% trisaccharide-substituted low molecular weight chitosans (branched chitosans) of various chain lengths were prepared and characterized as described [25,29]. Low molecular weight chitosans having number-average degrees of polymerization ($DP_n$) of 34, 50 and 85 monomer units were used throughout. The chain length distributions were analysed by size exclusion chromatography with a multi-angle laser light scattering (SEC-MALLS).

2.4. Cells

The human embryonic kidney cell line HEK 293 (293 cells) was obtained from ATCC, Rockville, Md., USA. Stably luciferase-expressing HEK 293 (293-Luc cells) that express firefly luciferase was a gift from Dr. Paavo Honkakoski, Department of Pharmaceutics, University of Kuopio, Finland [30]. Stably luciferase-expressing ovarian carcinoma cell line (SKOV-3-Luc) was also a gift from Dr. Achim Aigner, Department of Pharmacology and Toxicology, Philipps-University Marburg, Germany [17]. All cells were maintained according to the suppliers' recommendations.

2.5. Formulation of siRNA Complexes

Chitosan stock solutions (0.2 mg/ml) were prepared by dissolving chitosan in sterile MilliQ water at pH 6.2 followed by sterile filtration. Chitosan complexes were formulated by adding chitosan and then siRNA stock solutions or siRNA/pDNA (in case of co-transfection) to sterile MilliQ water during intense stirring on a vortex mixer (Heidolph REAX 2000, level 4, Kebo Lab, Spånga, Sweden) as described [25]. The following amounts of the different chitosans were used per μg pDNA or siRNA to prepare chitosan complexes at a charge ratio of 1:1 (+/−): 0.58 μg of linear chitosans, 0.69 μg of chitosans substituted with 7% A-A-M (branched chitosans) [25, 27]. siRNA complexes of PEI were prepared by adding PEI solutions to siRNA stock solutions or to siRNA/pDNA (in the case of transfection) during intense stirring on a vortex mixer as described [31]. The formulations were left for approximately 10 min. at room temperature before transfection. To form LF2000 complexes, siRNA stock solutions or siRNA/pDNA (in case of co-transfection) were added to chitosan solutions during intense stirring on a vortex mixer. Both siRNA and LF2000 solutions were diluted with the transfection medium OptiMEM I. LF2000 complexes were left for approximately 30 min. at room temperature before transfection. Based on preliminary experiments, a charge ratio of 15:1 (+/−) for PEI complexes and a weight ratio of 2:1 (+/−) for LF2000 complexes were selected and used throughout (data not shown).

2.6. Gel Retardation Assay

The physical stability of the siRNA complexes was studied using the agarose gel retardation assay. 4% agarose (MetaPhor® Agarose, Cambrex Bio Science Rockland, Inc., Rockland, Me., USA) in 40 mM TAE buffer was used as described [25]. Protection of complexed siRNA against enzymatic degradation was studied after incubating the complexes with 1.5 U RNase A (Ambion, UK) for 30-90 minutes as described [18]. After the incubation, the complexes were dissociated with heparin (5 mg/ml) and the integrity of siRNA was examined using the agarose retardation assay. siRNA obtained from the stock solution was used as control.

2.7. Size Measurements of Chitosan Polyplexes

The size of the complexes was determined by photon correlation spectroscopy using Nanosizer ZS (Malvern Instruments, Malvern, UK) as described [25]. The complexes were prepared at a siRNA concentration of 5 μg/ml in MilliQ water. All measurements were performed at 25 C.

2.8. In vitro Transfection Experiments

Twenty-four hours before the transfection experiments, HEK 293 (293, 293-Luc) cells and SKOV-3-Luc cells were seeded in 96-well tissue culture plates (Costar, Cambridge, UK) to get cell confluency of 80-90% on the day of transfection. Transfections were carried out at pH 7.4 in serum-free medium (OptiMEM I Reduced Serum Media, Gibco/BRL Life Technologies AB, Täby, Sweden) or in the presence of 10% serum (FBS). Isotonicity (300 mOsm/kg) was obtained by the addition of mannitol. The cells were washed with pre-heated OptiMEM and 50 μl of the siRNA complex formulations was added to each well. In co-transfection experiments, 0.33 μg pDNA (pLuc or pGFP) per well was used. A mismatch (control) siRNA was included in all in vitro experiments. After 5 h incubation, the formulations were removed and 0.2 ml of fresh culture medium was added. The medium was changed every second day for experiments that exceeded two days. At pre-specified time points, ranging from 24 to 120 hours after transfection, the cells were washed with pre-heated PBS (pH 7.4), and lysed with luciferase lysis buffer (Promega, Madison, Wis.). The luciferase gene expression was then measured with a luminometer (Mediators PhL, Vienna, Austria). The amount of luciferase expressed was determined from a standard curve prepared with firefly luciferase (Sigma, St Louis, Mo.).

2.9. Intracellular Dehydrogenase Activity (MTT Method)

The effect of various siRNA formulations on the intracellular dehydrogenase activity (a measure of cellular toxicity) in 293-Luc cells was evaluated by the MTT method as described [32]. Briefly, 293-Luc cells were transfected as described above. After 5 h of transfection, MTT (3-(4,5-dimethylthiazol-2-yl)-2,5-diphenyl tetrazolium bromide) (Sigma, Deisenhofen, Germany) solution in phosphate buffered saline (PBS) was added. After 4 h, the formazan crystals were dissolved by adding 100 μl of acid-isopropanol (0.04 M HCL in isopropanol). Absorption was measured at 570 nm with a background correction at 690 using a plate reader (TECAN Safire², Tecan Austria GmbH, Grödig, Austria). The instrument was set to 0 absorbance with culture medium treated in the same way. Intracellular dehydrogenase activity of the treated cells was related to that of the control (untreated) cells, and calculated from the following equation:

% Relative Intracellular Dehydrogenase Activity=
[$A$ (test)*100/$A$ (control)], where A (test) and A (control) are the absorbance values of the treated and control cells, respectively. In another setup, the cells were allowed to grow in culture medium for 24 h after transfection. Then, they were treated with the MTT reagent to test delayed toxicity of various formulations.

2.10. Data Analysis

The experiments were performed on a minimum of two occasions using quadruplicate samples. All data are expressed as mean values±standard deviation. Statistical differences between mean values were investigated using ANOVA. Differences between group means were considered significant at p<0.05.

Physical Stability and Enzymatic Protection

We first investigated the ability of linear and branched chitosan oligomers of various chain lengths to form stable complexes with siRNA in the gel retardation assay. Only complexes formulated with the longer, linear oligonucleotides with higher charge ratios retained the siRNA at pH 8.0, which is a commonly used pH for electrophoresis buffers (FIG. 1A). The linear low molecular weight chitosans having a number-average degree of polymerization ($DP_n$) of 85 monomer units ($DP_n85$) provided the highest physical stability at all the charge ratios tested. In contrast, when the pH of the gel buffer was lowered to 7.4, all the low molecular weight chitosans tested were able to form stable complexes with the siRNA. The reduced physical stability of siRNA formulations of branched and shorter chitosan oligomers at elevated pH values suggests that a higher charge density of the polycation and a stronger interaction with the siRNA are required to form physically stable complexes compared to previously optimized pDNA complexes formulated with low molecular weight chitosans [25, 27].

Since enzymatic degradation can be a limiting factor for gene silencing activity, we also investigated the ability of the selected low molecular weight chitosans to protect siRNA from enzymatic degradation by RNase A (incubation periods of 30-90 minutes were used).

In accordance with gene delivery requirements, all low molecular weight chitosans tested as well as the positive controls (PEI and LF2000) provided protection against enzymatic degradation compared to naked siRNA, which was completely degraded by RNase A (FIG. 1B). A longer incubation time with heparin (2 h) was needed to disrupt the complexes formulated with linear $DP_n85$ and LF2000 reflecting enhanced physical stability compared to the other polycations tested (data not shown).

Particle Size

Since the particle size of siRNA formulations can greatly affect their tissue distribution and cellular uptake, we therefore investigated the particle size of siRNA complexes formulated with low molecular weight chitosans. Table 1 shows that low molecular weight chitosans self-assembled with siRNA into nanosized particles (34-86 nm). The size of the resulting particles was dependent on the +/− charge ratios of the components. While small particle sizes (34-46 nm) were obtained at the lowest charge ratio 10:1 (+/−), the use of higher charge ratios resulted in relatively larger particles sizes (61-86 nm). Particle size was determined by photon correlation spectroscopy.

TABLE 1

|  | A/P 10 | A/P 30 | A/P 60 |
| --- | --- | --- | --- |
| DPn 18 | 38.1 ± 1.2 | 54.5 ± 0.1 | 62.5 ± 3.7 |
| DPn 34 | 37.7 ± 0.5 | 53.1 ± 0.9 | 68.2 ± 3.0 |
| DPn 50 | 34.0 ± 0.5 | 51.7 ± 1.2 | 63.6 ± 1.1 |
| DPn 85 | 37.4 ± 1.1 | 51.6 ± 3.3 | 61.0 ± 2.5 |
| DPn 34-AAM-7% | 38.5 ± 0.8 | 50.8 ± 0.4 | 68.9 ± 2.7 |
| DPn 85-AAM-7% | 46.0 ± 2.5 | 69.9 ± 1.7 | 86.1 ± 2.9 |

Comparison of the Silencing of Co-Transfected and Stably-Expressed Target

Since in most in vitro experiments siRNA molecules are delivered simultaneously with their pDNA targets (co-transfection), we first tested the efficiency of low molecular weight chitosans to deliver a package of pDNA coding for firefly luciferase reporter (pLuc) together with a siRNA that targets the same reporter sequence (siRNA-Luc) using a mismatch (non-silencing)siRNA as a control. The transfection was carried out in 293 cells (not expressing luciferase reporter) under optimized transfection conditions of pDNA dose, most efficient low molecular weight chitosans and charge ratios, which were optimized for pDNA delivery in our lab [27]. siRNA-Luc delivered by branched $DP_n34$ chitosan oligomers or LF2000 lead to a significant knockdown in luciferase expression (85-90%) compared to the control formulations (only pLuc) (FIG. 2A). A non-significant inhibition in luciferase expression was observed with the mismatch siRNA for both delivery systems. However, when the siRNA-Luc was instead exclusively delivered under the same conditions by the selected polycations to 293-Luc cells that stably express luciferase (a case which is more relevant to gene silencing applications), a very low luciferase silencing activity was obtained, and higher siRNA concentrations were required to obtain a significant silencing in luciferase expression (FIG. 2B).

To investigate if the co-transfection technique could have an effect on the gene silencing activity in the 293-Luc cells, an irrelevant plasmid (pGFP) was incorporated in the same siRNA-Luc formulations tested above. Similarly to the pattern obtained in 293 cells, branched chitosan oligomers, PEI and LF2000 mediated a significant knockdown (40-85%) in luciferase expression with the lowest siRNA concentrations (1-30 ng/well, equivalent to 1.5-40 nM/well) (FIG. 2C). The incorporation of pDNA in the siRNA formulations (co-transfection) resulted in a positive effect on the gene silencing activity. These results suggest that the formulation requirements for siRNA delivery differ from those of pDNA, and there are important parameters to be characterized for successful siRNA delivery by polycations in vitro.

Influence of the Structural Variables of Low Molecular Weight Chitosans and Formulation Parameters on the Gene Silencing Activity a) Chain Length, Backbone Branching and Charge Ratios In order to examine the effect of chitosan structure and the formulation parameters on siRNA delivery by low molecular weight chitosans, we first tested the influence of chain length, branching and charge ratio on the in vitro silencing of luciferase expression mediated by siRNA complexes in 293-Luc cells. For linear chitosans, chitosans with chain lengths longer than 34 monomer units mediated significant luciferase silencing independently on the charge ratio (FIG. 3A). The luciferase silencing mediated by complexes formulated with the branched chitosan oligomers was dependent on both the charge ratio and the chain length (FIG. 3B). For the longer branched chitosan oligomers, the higher charge ratios can compensate for the negative effect of the branching (substitution) of the chitosan backbone. These results emphasize that a high charge density of low molecular weight chitosans will not only yield physically stable complexes but also efficient siRNA formulations in vitro.

b) siRna Concentration and the Relative efficiency of Linear Low Molecular Weight Chitosans In the next step, the effect of the siRNA concentration on the luciferase silencing activity of complexes formulated with various linear low molecular weight chitosans (at constant charge ratios) was investigated in 293-Luc cells. With the lowest siRNA concentrations (15-50 ng/well, equivalent to 22-73 nM/well), linear $DP_n85$ complexes demonstrated the highest potency by knocking down the luciferase expression by 72-95% of the control untreated cells (FIG. 4). With the exception of $DP_n18$, complexes of the tested linear chitosans showed comparable luciferase silencing profiles when the siRNA concentration was increased from 70 to 300 ng/well (103-440 nM/well). The higher potency of the complexes formulated with linear, longer chain low molecular weight chitosans supports the role of the physical stability of siRNA formulations in achieving the highest gene silencing activity.

In vitro Transfection in the Presence of Serum

We also investigated the effect of serum in the transfection medium on the efficiency of various siRNA formulations. siRNA complexes formulated with linear chitosans having a range of DP values of 34-85 monomer units and branched $DP_n85$ chitosan oligomers retained their gene silencing activity in 293-Luc cells in the presence of 10% serum (FIG. 5). In contrast, the gene silencing activity of siRNA complexes formulated with PEI and LF2000 was compromised. One possible reason for the compromised efficiency is particle aggregation during transfection.

Cellular Toxicity in vitro

To ensure that the higher luciferase silencing efficiency was not a result of increased cellular toxicity, we investigated the effect of various polycation complexes formulated with a relatively high concentration of siRNA (150 nM) on the cellular morphology and the intracellular dehydrogenase activity using the MTT method. After 5 h of transfection, siRNA complexes formulated with linear $DP_n85$, no effect on cell morphology and intracellular dehydrogenase activity (a measure of cellular toxicity) was observed (FIG. 6). In contrast, a significant toxic effect was observed with PEI and LF2000, with the highest toxicity for linear PEI. While cells treated with LF2000 complexes restored their intracellular dehydrogenase activity after 24 h, cells treated with PEI displayed a further reduction in dehydrogenase activity after 24 h. These results demonstrate that the acute cellular toxicity of linear $DP_n85$ low molecular weight chitosans was lower than that of PEI and LF2000 even when relatively high concentrations of siRNA were used.

Kinetics of RNAi in vitro

Finally, the time course of luciferase silencing following the delivery of siRNA-Luc to 293-Luc cells was investigated. Low molecular weight chitosans having a range of DP values of 34-85 monomer units, PEI and LF2000 were tested. $DP_n18$ chitosans were not included because they were less efficient than the longer chitosans (FIG. 4). siRNA complexes formulated with linear DPn85 mediated an early onset of luciferase silencing where a significant effect was detected after 1 day (70%), reaching a maximum (92%) after 2 days (FIG. 7A). The gene silencing activity was sustained for 5 days suggesting stable release of intact siRNA intracellularly. Branched chitosan oligomers demonstrated less efficient luciferase silencing kinetics compared to their linear counterparts (FIG. 7B). LF2000 and PEI showed a lower gene silencing effect than that mediated by low molecular weight chitosans (FIG. 7C). The luciferase silencing kinetics in another cell line, SKOV-3-Luc, gave results similar to those in 293-Luc cells (FIG. 7D).

REFERENCES

[1] Meister G, Tuschl T, Mechanisms of gene silencing by double-stranded RNA, Nature. 431(7006) (2004) 343-9.

[2] Sachse C, Krausz E, Kronke A, Hannus M, Walsh A, Grabner A, Ovcharenko D, Dorris D, Trudel C, Sonnichsen B and others, High-throughput RNA interference strategies for target discovery and validation by using synthetic short interfering RNAs: functional genomics investigations of biological pathways, Methods Enzymol. 392((2005) 242-77.

[3] Dallas A, Vlassov A V, RNAi: a novel antisense technology and its therapeutic potential, Med Sci Monit. 12(4) (2006) RA67-74.

[4] Cejka D, Losert D, Wacheck V, Short interfering RNA (siRNA): tool or therapeutic?, Clin Sci (Lond). 110(1) (2006) 47-58.

[5] Burkhardt B R, Lyle R, Qian K, Arnold A S, Cheng H, Atkinson M A, Zhang Y C, Efficient delivery of siRNA into cytokine-stimulated insulinoma cells silences Fas expression and inhibits Fas-mediated apoptosis, FEBS Lett. 580 (2) (2006) 553-60.

[6] Devi G R, siRNA-based approaches in cancer therapy, Cancer Gene Ther. (2006).

[7] Nishitsuji H, Kohara M, Kannagi M, Masuda T, Effective Suppression of Human Immunodeficiency Virus Type 1 through a Combination of Short- or Long-Hairpin RNAs Targeting Essential Sequences for Retroviral Integration, J Virol. 80(15) (2006) 7658-66.

[8] Sioud M, On the delivery of small interfering RNAs into mammalian cells, Expert Opin Drug Deliv. 2(4) (2005) 639-51.

[9] Elmen J, Thonberg H, Ljungberg K, Frieden M, Westergaard M, Xu Y, Wahren B, Liang Z, Orum H, Koch T and others, Locked nucleic acid (LNA) mediated improvements in siRNA stability and functionality, Nucleic Acids Res. 33(1) (2005) 439-47.

[10] Chen X, Dudgeon N, Shen L, Wang J H, Chemical modification of gene silencing oligonucleotides for drug discovery and development, Drug Discov Today. 10(8) (2005) 587-93.

[11] Lorenz C, Hadwiger P, John M, Vornlocher H P, Unverzagt C, Steroid and lipid conjugates of siRNAs to enhance cellular uptake and gene silencing in liver cells, Bioorg Med Chem Lett. 14(19) (2004) 4975-7.

[12] Dalby B, Cates S, Harris A, Ohki E C, Tilkins M L, Price P J, Ciccarone V C, Advanced transfection with Lipofectamine 2000 reagent: primary neurons, siRNA, and high-throughput applications, Methods. 33(2) (2004) 95-103.

[13] Hassani Z, Lemkine G F, Erbacher P, Palmier K, Alfama G, Giovannangeli C, Behr J P, Demeneix B A, Lipid-mediated siRNA delivery down-regulates exogenous gene expression in the mouse brain at picomolar levels, J Gene Med. 7(2) (2005) 198-207.

[14] Santel A, Aleku M, Keil O, Endruschat J, Esche V, Fisch G, Dames S, Loffler K, Fechtner M, Arnold W and others, A novel siRNA-lipoplex technology for RNA interference in the mouse vascular endothelium, Gene Ther. (2006).

[15] Pirollo K F, Zon G, Rait A, Zhou Q, Yu W, Hogrefe R, Chang E H, Tumor-targeting nanoimmunoliposome complex for short interfering RNA delivery, Hum Gene Ther. 17(1) (2006) 117-24.

[16] Jaaskelainen I, Peltola S, Honkakoski P, Monkkonen J, Urtti A, A lipid carrier with a membrane active component and a small complex size are required for efficient cellular delivery of anti-sense phosphorothioate oligonucleotides, Eur J Pharm Sci. 10(3) (2000) 187-93.

[17] Urban-Klein B, Werth S, Abuharbeid S, Czubayko F, Aigner A, RNAi-mediated gene-targeting through systemic application of polyethylenimine (PEI)-complexed siRNA in vivo, Gene Ther. 12(5) (2005) 461-6.

[18] Zhou J, Wu J, Hafdi N, Behr J P, Erbacher P, Peng L, PAMAM dendrimers for efficient siRNA delivery and potent gene silencing, Chem Commun (Camb). 22) (2006) 2362-4.

[19] Leng Q, Scaria P, Zhu J, Ambulos N, Campbell P, Mixson A J, Highly branched HK peptides are effective carriers of siRNA, J Gene Med. 7(7) (2005) 977-86.

[20] Regnstrom K, Ragnarsson E G, Koping-Hoggard M, Torstensson E, Nyblom H, Artursson P, PEI—a potent, but not harmless, mucosal immuno-stimulator of mixed T-helper cell response and FasL-mediated cell death in mice, Gene Ther. 10(18) (2003) 1575-83.

[21] Chen H T, Neerman M F, Parrish A R, Simanek E E, Cytotoxicity, hemolysis, and acute in vivo toxicity of dendrimers based on melamine, candidate vehicles for drug delivery, J Am Chem Soc. 126(32) (2004) 10044-8.

[22] Omidi Y, Barar J, Akhtar S, Toxicogenomics of cationic lipid-based vectors for gene therapy: impact of microarray technology, Curr Drug Deliv. 2(4) (2005) 429-41.

[23] Roy K, Mao H Q, Huang S K, Leong K W, Oral gene delivery with chitosan—DNA nanoparticles generates immunologic protection in a murine model of peanut allergy, Nat Med. 5(4) (1999) 387-91.
[24] Koping-Hoggard M, Tubulekas I, Guan H, Edwards K, Nilsson M, Varum K M, Artursson P, Chitosan as a nonviral gene delivery system. Structure-property relationships and characteristics compared with polyethylenimine in vitro and after lung administration in vivo, Gene Ther. 8(14) (2001) 1108-21.
[25] Koping-Hoggard M, Varum K M, Issa M, Danielsen S, Christensen B E, Stokke B T, Artursson P, Improved chitosan-mediated gene delivery based on easily dissociated chitosan polyplexes of highly defined chitosan oligomers, Gene Ther. 11(19) (2004) 1441-52.
[26] Zhang W, Yang H, Kong X, Mohapatra S, San Juan-Vergara H, Hellermann G, Behera S, Singam R, Lockey R F, Mohapatra S S, Inhibition of respiratory syncytial virus infection with intranasal siRNA nanoparticles targeting the viral NS1 gene, Nat Med. 11(1) (2005) 56-62.
[27] Issa M M, Koping-Hoggard M, Tommeraas K, Varum K M, Christensen B E, Strand S P, Artursson P, Targeted gene delivery with trisaccharide-substituted chitosan oligomers in vitro and after lung administration in vivo, J Control Release. (2006).
[28] Elbashir S M, Harborth J, Lendeckel W, Yalcin A, Weber K, Tuschl T, Duplexes of 21-nucleotide RNAs mediate RNA interference in cultured mammalian cells, Nature. 411(6836) (2001) 494-8.
[29] Tommeraas K, Koping-Hoggard M, Varum K M, Christensen B E, Artursson P, Smidsrod O, Preparation and characterisation of chitosans with oligosaccharide branches, Carbohydr Res. 337(24) (2002) 2455-62.
[30] Honkakoski P, Jaaskelainen I, Kortelahti M, Urtti A, A novel drug-regulated gene expression system based on the nuclear receptor constitutive androstane receptor (CAR), Pharm Res. 18(2) (2001) 146-50.
[31] Boussif O, Lezoualc'h F, Zanta M A, Mergny M D, Scherman D, Demeneix B, Behr J P, A versatile vector for gene and oligonucleotide transfer into cells in culture and in vivo: polyethylenimine, Proc Natl Acad Sci USA. 92(16) (1995) 7297-301.
[32] Lappalainen K, Jaaskelainen I, Syrjanen K, Urtti A, Syrjanen S, Comparison of cell proliferation and toxicity assays using two cationic liposomes, Pharm Res. 11(8) (1994) 1127-31.
[33] Howard K A, Rahbek U L, Liu X, Damgaard C K, Glud S Z, Andersen M O, Hovgaard M B, Schmitz A, Nyengaard J R, Besenbacher F and others, RNA Interference in Vitro and in Vivo Using a Novel Chitosan/siRNA Nanoparticle System, Mol Ther. (2006).
[34] Katas H. Alpar H O, Development and characterisation of chitosan nanoparticles for siRNA delivery, J Control Release. (2006).
[35] Janes K A, Calvo P, Alonso M J, Polysaccharaide colloidal particles as delivery systems for macromolecules. Adv Drug Deliver Rev. 47(1) (2001) 83-97.

What is claimed is:

1. A composition comprising complexes of:
    (a) low molecular weight chitosan having a Degree of Polymerization ($DP_n$) in the range between 30 and 300 and where the degree of deacetylation of the low molecular weight chitosan is greater than 99%; and
    (b) siRNA;
wherein said complexes comprise particles having a particle size less than 100 nm.

2. The composition of claim 1, wherein the low molecular weight chitosan is obtained from high molecular weight chitosan using chemical or enzymatic methods.

3. The composition of claim 1, wherein the composition essentially has a net positive charge ratio.

4. The composition of claim 1 wherein the low molecular weight chitosan is derivatized with targeting ligands and stabilizing agents.

5. The composition of claim 1, wherein the siRNA comprises a silencing sequence that will express its function when introduced into a host cell.

6. The composition of claim 1, wherein the composition has a pH in the range of 3.5 to 8.0.

7. The composition of claim 6, wherein the composition has a pH in the range of 7.1 to 7.6.

8. The composition of claim 1, wherein said Degree of Polymerization ($DP_n$) is in the range between 34 and 85.

9. The composition of claim 1, wherein said Degree of Polymerization ($DP_n$) is 85.

10. A method of preparing the composition of claim 1, comprising the steps of:
    (a) exposing the low molecular weight chitosan to an aqueous solvent;
    (b) mixing the aqueous solution of step (a) with the siRNA in an aqueous solvent; and
    (c) maintaining the pH of the composition in the range of 3.5-8.0.

11. The method of claim 10 further comprising reducing the volume of the product solution produced in step (b) to obtain a desired concentration of the composition.

* * * * *

```
                              SEQUENCE LISTING

<160> NUMBER OF SEQ ID NOS: 4

<210> SEQ ID NO 1
<211> LENGTH: 21
<212> TYPE: DNA
<213> ORGANISM: Artificial
<220> FEATURE:
<223> OTHER INFORMATION: synthetic siRNA sequence
<220> FEATURE:
<221> NAME/KEY: misc_feature
<222> LOCATION: (1)..(21)
<223> OTHER INFORMATION: bases 1-19 are RNA, bases 20-21 are DNA

<400> SEQUENCE: 1
cuuacgcuga guacuucgat t                                                 21

<210> SEQ ID NO 2
<211> LENGTH: 21
<212> TYPE: DNA
<213> ORGANISM: Artificial
<220> FEATURE:
<223> OTHER INFORMATION: Synthetic siRNA sequence
<220> FEATURE:
<221> NAME/KEY: misc_feature
<222> LOCATION: (1)..(21)
<223> OTHER INFORMATION: bases 1-19 are RNA; bases 20-21 are DNA

<400> SEQUENCE: 2
ucgaaguacu cagcguaagt t                                                 21

<210> SEQ ID NO 3
<211> LENGTH: 21
<212> TYPE: RNA
<213> ORGANISM: Artificial
<220> FEATURE:
<223> OTHER INFORMATION: synthetic siRNA sequence
```

```
<400> SEQUENCE: 3
uagcgacuaa acacaucaau u                                              21

<210> SEQ ID NO 4
<211> LENGTH: 21
<212> TYPE: RNA
<213> ORGANISM: Artificial
<220> FEATURE:
<223> OTHER INFORMATION: synthetic siRNA sequence

<400> SEQUENCE: 4
uugauguguu uagucgcuau u                                              21
```